United States Patent [19]

Platt

[11] Patent Number: 4,820,629

[45] Date of Patent: Apr. 11, 1989

[54] IMMUNOASSAY FOR ANTIBODIES TO PSEUDORABIES VIRUS USING MEDIUM-ELABORATED VIRAL ANTIGENIC FACTOR

[75] Inventor: Kenneth B. Platt, Ames, Iowa

[73] Assignee: Iowa State University Research Foundation, Inc., Ames, Iowa

[21] Appl. No.: 790,130

[22] Filed: Oct. 22, 1985

Related U.S. Application Data

[63] Continuation-in-part of Ser. No. 499,204, May 31, 1983, abandoned.

[51] Int. Cl.$^4$ ...................... C12Q 1/70; G01N 33/535
[52] U.S. Cl. ........................................... 435/5; 435/7; 424/86; 424/89
[58] Field of Search .............................. 435/5, 7, 810; 424/86, 89, 93

[56] References Cited

U.S. PATENT DOCUMENTS 4,562,147 12/1985 Joo ........................................... 435/5
4,711,850 12/1987 Kit et al. .............................. 435/235

FOREIGN PATENT DOCUMENTS 0133200 2/1985 European Pat. Off. ................ 435/5

Primary Examiner—Margaret Moskowitz
Attorney, Agent, or Firm—Tilton, Fallon, Lungmus & Chestnut

[57] ABSTRACT

Swine serum is tested for antibodies to pseudorabies (PR) virus by an immunoassay using a specific supernatant-elaborated PR virus antigen which is antigenically distinct from the lectin-binding glycoproteins of PR virus.

1 Claim, No Drawings

IMMUNOASSAY FOR ANTIBODIES TO PSEUDORABIES VIRUS USING MEDIUM-ELABORATED VIRAL ANTIGENIC FACTOR

GRANT REFERENCE

The research work leading to this invention was funded in part under USDA-ARS Cooperative Agreement No. 58-519B-1-0999.

RELATED APPLICATION

This application is a continuation-in-part of copending application Ser. No. 499,204, filed May 31, 1983.

FIELD OF INVENTION, BACKGROUND AND PRIOR ART

The field of this invention relates to a method of using a diagnostic antigen preparation derived from pseudorabies (PR) virus. More specifically, the invention relates to the use of a diagnostic preparation, which is complementary to the antigen of a PR vaccine, thereby permitting PR virus carriers to be distinguished from vaccinated swine. For convenience of reference, the abbreviation "PR" is used herein to mean "pseudorabies."

Heretofore a diagnostic preparation for determining swine infection by PR virus has been prepared by solubilizing PR virus-infected cells with an aqueous solution of a nonionic detergent. This preparation contains all of the antigens of the virus. When used in a standard test procedure for the presence of serum antibodies to PR virus, such as the enzyme-linked immunosorbant assay (ELISA), swine found positive are assumed to be actual or potential carriers of the virus. However, positive reaction may be due to natural infection and recovery, or to vaccine immunization with whole killed virus, and the swine may not be carriers of the virus. A negative result, however, does permit the determination that the swine are noncarriers.

Sub-unit vaccines for pseudorabies have been developed and shown to be effective. These vaccines are prepared to contain less than the full complement of antigens from the virus, and, specifically, only the glycoprotein antigens of the virus. One method for preparing such a sub-unit vaccine is described in U.S. Pat. No. 4,470,967, entitled "Lectin-Containing Anti-Viral Vaccines for Domestic Animals and Method of Preparation." Example 1 of the cited patent relates specifically to a vaccine of this kind for pseudorabies.

A sub-unit vaccine for pseudorabies containing similar glycoprotein antigens can also be prepared by the method described in U.S. Pat. No. 4,493,825, entitled "Purified and Antigenically Selective Vaccines for Domestic Animals." Particular reference may be had to Examples I and II of the last-cited patent. But it should be understood that the disclosures of these patents are cited only by way of background, and that the details of preparing such subunit lectin-binding glycoprotein vaccines for pseudorabies are not an essential part of the disclosure of the present invention. However, it is one of the important advantages of the diagnostic antigenic preparation of this invention that it can be used as a complementary antigenic preparation with respect to the sub-unit vaccines of the above-cited patents, or of other sub-unit vaccines which are based on lectin-binding glycoproteins of PR virus.

In a prior publication, I have disclosed studies of the pseudorabies virus antigens. Platt, K. B., *Vet. Micro.* 7 (1982), 515–534. Pseudorabies virus, also known as Aujeszky's disease virus, was solubilized with an aqueous solution of a nonionic detergent. The full complement of antigens was studied and partially characterized, the antigens being divided into Groups I, II and III (see page 521). In separate experiments of the same study, the antigens which were adsorbed on a lectin-agarose gel column (the lectin retentate antigens) were studied. It was found that these were antigens of Group III (see page 524).

Erickson and Kaplan have studied protein synthesis of PR virus. *Virology* 5 (1973) 94–102. They reported that a protein produced by the PR virus was found in the culture medium and identified this protein by the designation "3a". In the procedure described (page 96, FIG. 2), the cells were infected with the PR virus, the medium was changed at four hours, the cells were then incubated with fresh medium for four more hours, and at eight hours post-infection the culture fluid was electrophoresed with detection of the 3a protein fraction. The 3a protein was found to be sulfated, and was tentatively classified as a mucopolysaccharide or protoglycan.

Erickson and Kaplan did not determine the degree of purity of the 3a protein, or whether the fraction identified was free from viral glycoproteins. Pennington and McCrae subsequently reported that PR virus will elaborate protein which is sulphated and glycosylated. *J. Gen. Virol.* (1977), 34:155–165. As described by these researchers, the polypeptide 89K is glycosolated very soon after synthesis of the polypeptide chain, and is then sulfated, reduced in size, and excreted. Pennington and McCrae classified protein 89K (assumed to be similar to Erickson and Kaplan protein 3a) as a glycoprotein. They reported that "significant amounts of non-glycosylated precursors were never observed in the medium." (Pennington et al., cited above, page 163.)

SUMMARY OF INVENTION

The medium-elaborated antigenic factor (MEA) used in the method of this invention has been shown to be like the Class I antigen group, as described in my prior publication (*Vet. Micro.* 7 (1982), 515–534). The abbreviation "MEA" is used herein to designate the medium-elaborated antigen which is prepared in accordance with the method of this invention. The Rf value of MEA as determined against human albumin in the absence of urea is about 1.0. Further, the antigenic factors of MEA are clearly different from the antigens of Groups II and III. The MEA may contain more than one protein, or may be a monomer or polymer of a single protein. Importantly, MEA is not a lectin-binding glycoprotein. MEA is the only antigenic factor related to the PR virus found in the medium external to the cells, providing that the medium is harvested at a critical intermediate time during the viral replication cycle there are no detectable antigens of Groups II and III present. The thus-harvested medium is therefore an ideal source for a complementary diagnostic antigen for use with swine which have been vaccinated with lectin binding glycoproteins of PR virus.

MEA is believed to be similar but not identical in anti-genic properties to the 3a protein described by Erickson and Kaplan (1973, cited above) and/or the protein 89K of Pennington and McCrae (1977, cited above). These researchers did not recognize that the primary medium-elaborated protein was in a different antigenic group than lectin-binding glycoproteins.

For the purposes of the present invention, the MEA protein is needed in a very high purity form. This requires collection of the broth containing the MEA at a defined time during infection of the cells. The optimum time for collection of the MEA is usually about 4 to 6 hours post-infection. Erickson and Kaplan discarded the four-hour broth and obtained their 3a protein from fresh broth in which the cells were cultured starting at four hours post-infection, the collection being made at 8 hours postinfection. Thus, the 4-hour broth was discarded and not recognized as a source of protein 3a in purer form. Pennington and McCrae did not even begin labeling the infected cells until 7 to 17 hours postinfection. No use was suggested for earlier collected culture medium.

DETAILED DESCRIPTION

The medium-elaborated antigen (MEA) used in the method of this invention can be produced by known culturing and viral replication procedures for PR virus. Such procedures have heretofore been described in the literature. For example, Platt, et al., *Archives Virolog.*, 60 (1979), 13-23.

For example, a standard roller bottle apparatus may be used. A cell-line is selected, such as kidney cells adapted for in vitro propagation, the cells being ones in which PR virus replicate freely. The cells are introduced into the roller bottles together with a suitable aqueous medium, such as Eagle's minimum essential medium. During the initial growth of the cells it is preferred, as in prior practice, to incorporate fetal calf serum in the medium, such as at a level of 10% by volume. After the cells have been grown to form a monolayer in the bottles, the medium is removed, and the cells are infected with an inoculant solution containing live PR virus. The inoculant is left in contact with the cells for a sufficient time to obtain infection, such as about 90 minutes, and is then removed. The infected cells in the monolayer are then washed, such as with Earle's medium without fetal calf serum. After removal of the wash solution, additional medium free of fetal calf serum, such as Earle's medium, is added.

The infected cells are incubated in contact with the medium according to the usual practice until the viral replication has proceeded to an intermediate time in the viral replication cycle where the desired diagnostic antigenic factor (MEA) has accumulated in the medium. At that time, the incubation is interrupted, and the medium is removed to obtain the aqueous solution of the MEA for use as a diagnostic antigen. If desired, additional medium is then added, and the incubation is continued to the completion of the viral replication cycle. The virus can then be harvested in the usual way and employed to prepare vaccine preparations, such as particularly sub-unit vaccines containing the lectin-binding glycoprotein antigens as referred to above.

Cell lines of adapted swine or bovine kidney cells have been found particularly desirable for replication of PR virus. One suitable cell line is the PK-15 cell line obtainable from the National Veterinary Services Laboratory in Ames, Iowa. Another suitable cell line is the MDBK cell line which is obtainable from the American Type Culture Collection at Rockville, Md., under Accession No. CCL-22. However, any cell line can be employed in which the PR virus replicates.

The optimum time for harvesting MEA can be related to an established culturing procedure. For example, with an infection multiple of 5, the medium can be advantageously collected around 6 hours after initiation of the infection. Where a multiple of 10 infectious virus particles per cell is employed, it appears that the optimum time for collecting the medium will be around 4 hours. It is not desirable to change the medium during MEA elaboration, since this is wasteful of MEA. Further, the early MEA is believed to be the purest antigenically--being free from lectin-binding glycoproteins.

In general, the cells may be infected with multiples of from 3 to 12 virus per cell, and the medium containing the antigen may be harvested within the time period from 2 to 8 hours after the start of the replication. It appears that the optimum time for antigen harvest is usually 4 to 6 hours after infection of the cells, but the exact time of maximum yield will be determined in part by the multiplicity of virus infection used. Further, if too high a multiplicity is used it is difficult to obtain the MEA in relatively pure form, other antigens of Group II and III being present in admixture with MEA. Therefore, it is preferred to use a low multiplicity such as a multiplicity of 5 or less and to collect the MEA at about 6 hours post cell infection. It should be understood that while these infection levels and collection times are set out as preferred examples, the method of this invention is not limited thereto.

Incubation conditions both for the growing of the cells and for the replication of the virus may be those which are usually employed, for example, in an incubation temperature of around 37° C., etc.

After separation of the MEA-containing aqueous medium from the cells, some further processing steps are desirable, although not essential. For example, the medium may be centrifuged or filtered to remove cell debris. If desired, the centrifugation may be under very high gravity, effective for pelleting virus. Residual virus in the medium can thereby also be removed. Further, to be sure that no live virus carry through in the diagnostic antigen, it can be heated at a suitable temperature and time for killing the virus, such as at a temperature of 56° C. for one hour. Such heating inactivates the PR virus but does not significantly denature the MEA protein.

Following the solids removal and heat treatment as described, the solution of the MEA may be concentrated, if desired, such as by ultrafiltration. Concentration is not required, however, since the medium from a single roller bottle will contain sufficient MEA for several hundred assays.

The MEA preparation described above can be used in standard immunoassay procedures, such as particularly the enzyme-linked immunosorbent assay (ELISA) procedure.

The method of this invention and the MEA antigenic preparation used therein is further illustrated by the following experimental examples.

EXAMPLE I

The diagnostic antigen of this invention (MEA) is prepared as follows:

1. Confluent cell monolayers are prepared in plastic roller bottles. The cell type used is PK-15 or the MDBK cell lines. Other cell types that support the replication of pseudorabies virus may also be used.

2. The cell monolayers are inoculated with pseudorabies virus at a multiplicity of infection of 1 to 5 and incubated at 37° C. for 90 minutes.

3. The virus inoculum is then removed from the cell monolayers.

4. The cell monolayers are washed three times with minimum essential medium containing antibiotics and free of serum supplement.

5. The washed monolayers are then supplied with serumfree minimum essential medium containing antibiotic. The medium is supplied at a rate of 40 ml per 850 $cm^2$ roller bottle.

6. The infected cell monolayers are then reincubated at 37° C.

7. The serum-free medium containing the medium-elaborated antigen (MEA) is removed from the cell containers between 4 and 6 hours following virus inoculation. The optimum time for harvesting must be determined by trial and error.

8. New serum-free medium is added to the cell monolayers which are ultimately used as a source of antigen for the subunit vaccines described earlier.

9. The harvested MEA is clarified by low speed centrifugation then heated to 56° C. and maintained at this temperature for 30 to 60 minutes for the purpose of destroying potential virus activity.

10. The MEA is then filtered through a 220 nm pore size Milipore filter.

11. The filtrate is then concentrated by ultrafiltration for ease in storage or used directly in the undiluted state as diagnostic antigen.

EXAMPLE II

MEA antigen prepared as described in Example I can be employed in enzyme-linked immunosorbent assays (ELISA) as follows:

1. One hundred μl of optimally diluted medium-elaborated antigen (MEA) in 0.02M carbonate/bicarbonate buffer pH 9.6 is added to alternate rows of individual wells of polyvinyl chloride (PVC) Microtiter plates (Dynatech Laboratories, Alexandria, VA).

The same amount of sham antigen consisting of maintenance medium of nonvirus infected cells is then added to the remaining rows of empty wells.

The correct dilution of sham antigen to be used is that dilution which when added to wells and ultimately reacted with known negative serum gives the same absorbance reading as that which occurs when the same negative serum is reacted with MEA.

2. The PVC plates are then incubated 3 hours at 37° C. for at least 18 h at 4° C. to permit the antigen to adsorb to the plate.

3. Immediately prior to use the antigen coated plates are washed 3 times with phosphate buffered saline 0.01M, pH 7.2 containing 0.05% Tween 20.

4. Test and appropriate control serums are diluted 1:20 in 0.05M Tris buffer pH 7.4 containing 150 mM NaCl, 0.01 mM EDTA, 0.05% Tween 20 and 1.0% bovine serum albumin.

5. One hundred μl of individually diluted serums are added to MEA-coated and sham antigen-coated wells in duplicate.

6. Plates are then incubated at 37° C. for 30 min and subsequently washed with PBS.

7. Fifty μl of goat anti-porcine IgG conjugated to horseradish peroxidase is added to individual wells and the plate are reincubated at 25° C. for 30 minutes.

8. The plates are then washed with PBS and 100 μl of enzyme substrate is added to individual wells.

The enzyme substrate is prepared by adding 400 μl of 1% hydrogen peroxide and 100 μl of a 40 mM solution of 2-2'azino-di(3-ethylbenzthiazoline-6-sulfonate) to 10 ml of 0.05M citric acid pH 4.0.

9. The color reaction following the addition of enzyme substrate is allowed to develop at 25° C. for 20 minutes and then stabilized by adding 50 μl of a 1:400 dilution of 48% concentrated reagent grade hydrofluoric acid.

10. The mean absorbance value for the duplicate wells containing MEA and the sham antigen is determined with the Dynatech MR 580 ELISA microplate reader using a test filter wavelength of 405 nm and a reference filter wavelength of 405 nm.

11. The ratio of the mean absorbance values of an individual serum reacting with MEA to the mean absorbance value obtained from reacting the same serum with sham antigen was determined. Ratios of 1.75 or greater are considered to indicate the presence of antibody to MEA.

EXAMPLE III

This experiment demonstrates the uniqueness of MEA as an antigen to be used in an enzyme-linked immunosorbent assay (ELISA) for the differentiation of vaccinated pigs that have been infected with pseudorabies virus from vaccinated pigs that have not been infected with the virus. The MEA was prepared as described in Example I and the ELISA tests were carried out as described in Example II.

Twelve pigs were vaccinated with 2 doses of a subunit vaccine consisting of lectin-bound glycoprotein antigens. Ten pigs from the same litters were maintained as uninoculated controls. Three weeks after the second vaccine dose was given serum were collected from all pigs. Each pig was then challenged intranasally with $10^{8.5}$ plaque forming units of virulent PR virus. Eleven of the 12 vaccinated pigs survived the challenge. In contrast all 10 control pigs died within eight days of the challenge.

Serums were collected from all survivors on the day the first vaccine dose was given, on the day of virus challenge, and at 10, 21 and 62 days post challenge. Each serum sample was then assayed for the presence of PR virus specific antibody by the ELISA test utilizing (a) the MEA and (b) conventional antigen prepared by solubilizing whole virus-infected cells. The principal difference between these antigens is that the MEA does not contain antigens that are present in the subunit vaccine whereas the conventional antigen does contain the antigens found in the vaccine.

The results of the ELISA tests utilizing each antigen are summarized in Table A. Test values (i.e., absorbance ratios) ranging up to 1.75 are considered negative. Values that exceed 1.75 indicate the presence of antibody specific for PR virus antigens. These data indicate that vaccinates were free of antibody on the day (−42) that they received the first vaccine dose. The data also shows that vaccinates were still negative for PR virus antibody on the day of virus challenge (day 0) when the ELISA test was run with MEA. However, when the ELISA test was run with conventional antigen PR virus specific antibody was detected in all vaccinates, i.e., absorbance ratios exceeded 1.75. Following challenge, antibody to PR virus was detected in the vaccinates by the ELISA test when either MEA or conventional antigen was used.

These results clearly demonstrate that MEA can be used to detect PR virus infections in the pig. Furthermore, because MEA does not contain vaccine antigen it can be used to differentiate virus-infected subunit-vaccinated pigs from subunit-vaccinated pigs that have not been infected with the virus.

TABLE A

Antibody response of vaccinated and control pigs before and after pseudorabies virus challenge as determined by the ELISA with MEA and conventional diagnostic antigen

| Pigs | Antigen | Days$^a$ pre and post challenge | | | | |
| --- | --- | --- | --- | --- | --- | --- |
| | | −42 | 0 | 10 | 21 | 62 |
| Vaccinates$^b$ | MEA | 1.1 (±.2)$^c$ | 1.1 (±.1) | 5.1 (±.7) | 5.4 (±.3) | 3.8 (±.2) |
| | CONVENTIONAL | 1.1 (±.1) | 3.9 (±.3) | 6.4 (±.9) | 6.5 (±.2) | 6.6 (±.6) |
| Controls | MEA | — | 1.1 (±.1) | — | — | — |
| | CONVENTIONAL | — | 1.0 (±.1) | — | — | — |

$^a$Day −42 is the day that the vaccinates received the first vaccine dose. Day 0 is the day that all pigs were nasally challenged with pseudorabies virus.
$^b$N = 12 for vaccinates through day 0, then N = 11. N = 10 controls.
$^c$Values = the ratio of the absorbance obtained with MEA or conventional antigen to the absorbance obtained with sham antigen. Ratios >1.75 indicate the presence of pseudorabies-specific antibody.

I claim:

1. The method for testing swine serum to determine the presence of antibodies to pseudorabies virus as distinguished from antibodies to lectin-binding pseudorabies glycoproteins in which an enzyme-linked immunosorbent assay is is performed on the swine serum using a pseudorabies virus antigen preparation, wherein the improvement comprises employing as said pseudorabies antigen preparation a solution containing a medium-elaborated antigenic factor which is antigenically distinct from the lectin-binding glycoproteins of pseudorabies virus, said medium-elaborated antigenic factor solution having been prepared by the following steps:

(a) growing mammalian kidney cells adapted for in vitro propagation to produce a cell culture;

(b) infecting the cell culture with replicable pseudorabies virus using about 3 to 12 virus per cell;

(c) replicating the pseudorabies virus in the infected cells in contact with an aqueous culture medium without changing the medium, said medium being free of fetal calf serum;

(d) interrupting the virus replication at an intermediate time in the replication cycle of from about 4 to 6 hours after the start of the replication when the medium-elaborated antigenic factor is present in the medium in essentially antigenically pure form; and (e) separating the culture medium from the infected cells to obtain said aqueous solution of the medium-elaborated antigenic factor.

* * * * *